US008945623B2

(12) United States Patent
Roy et al.

(10) Patent No.: US 8,945,623 B2
(45) Date of Patent: Feb. 3, 2015

(54) COMPOSITIONS COMPRISING BIOMEMBRANE SEALING AGENT FOR TREATMENT OF NEURONAL INJURY, AND METHODS OF USE

(75) Inventors: Josee Roy, Memphis, TN (US); William F. McKay, Memphis, TN (US); Jeffrey C. Marx, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1497 days.

(21) Appl. No.: 11/418,152

(22) Filed: May 3, 2006

(65) Prior Publication Data
US 2007/0259044 A1 Nov. 8, 2007

(51) Int. Cl.
| | |
|---|---|
| A61K 38/20 | (2006.01) |
| A61K 38/18 | (2006.01) |
| A61K 38/11 | (2006.01) |
| A61K 38/05 | (2006.01) |
| A61K 31/65 | (2006.01) |
| A61K 31/56 | (2006.01) |
| A61K 9/14 | (2006.01) |
| A61K 9/00 | (2006.01) |
| A61K 33/06 | (2006.01) |
| A61K 47/10 | (2006.01) |

(52) U.S. Cl.
CPC .............. *A61K 9/0019* (2013.01); *A61K 31/56* (2013.01); *A61K 31/65* (2013.01); *A61K 33/06* (2013.01); *A61K 47/10* (2013.01)
USPC ............ 424/486; 514/1.1; 514/171; 514/152; 514/18.1; 514/423; 514/560; 514/548; 424/85.2; 607/2

(58) Field of Classification Search
USPC ........... 424/486, 85.2; 514/11, 171, 152, 423, 514/560, 548, 18.1; 607/2
See application file for complete search history.

(56) References Cited

U.S. PATENT DOCUMENTS

| | | | |
|---|---|---|---|
| 3,026,248 | A | 3/1962 | Noseworthy et al. |
| 4,020,162 | A | 4/1977 | Ghilardi et al. |
| 4,451,447 | A | 5/1984 | Kaplan et al. |
| 4,462,984 | A * | 7/1984 | Mizuno et al. ............. 514/772.7 |
| 5,605,687 | A | 2/1997 | Lee et al. |
| 5,629,012 | A * | 5/1997 | Halskov ........................ 424/436 |
| 6,310,053 | B1* | 10/2001 | Patterson et al. ............. 514/152 |
| 7,582,680 | B1 | 9/2009 | Shi et al. |
| 7,837,987 | B2 | 11/2010 | Shi et al. |
| 2003/0118545 | A1 | 6/2003 | Shi et al. |
| 2004/0214790 | A1 | 10/2004 | Borgens |
| 2005/0069520 | A1 | 3/2005 | Shi et al. |
| 2005/0101597 | A1* | 5/2005 | Stephenson et al. ....... 514/223.5 |

FOREIGN PATENT DOCUMENTS

| | | |
|---|---|---|
| GB | 1250304 A | 10/1971 |
| GB | 1286351 A | 8/1972 |
| WO | WO01/28544 A | 4/2001 |
| WO | 02092107 | 11/2002 |

OTHER PUBLICATIONS

Borgens (Neurosurgery. Aug. 2001;49(2):370-8; abstract only).*
Lee JS, et. al (J Neurotrauma. May 2004;21(5):549-61; abstract only).*
Won SJ et al. (Cellular and Molecular Pathways of Ischemic Neuronal Death, J Biochem Mol Biol. Jan. 31, 2002;35(1):67-86).*
Kew, NC and Kemp, JA (Psychopharmacology 2005, vol. 159: 4-29).*
Inject: retrived from http://www.merriam-webster.com/dictionary/injectable. Retrived on Nov. 26, 2012.*
Ditor, et al.: "Effects of Polyethylene Glycol and Magnesium Sulfate Administration on Clinically Relevant Neurological Outcomes after Spinal Cord Injury in the rat", Journal of Neuroscience Research, 85:1458-1467, 2007.*
Polyethylene glycol 1500: retrieved from internet: (http://www.emdmillipore.com/chemicals/polyethylene-glycol-1500/MDA_CHEM-807489/p_1P2b.s1LvaMAAAEWruEfVhTI?CountryName=United+States+of+America. Retrieved on Jan. 7, 2014.*
PEG 1500 20%: retrieved from internet: http://www.sigmaaldrich.com/catalog/product/fluka/42876?lang=en&region=US. Retrieved on Jan. 7, 2014.*
Kaptanoglu et al., "Effects of magnesium sulphate in experimental spinal cord injury: evaluation with ultrastructural findings and early clinical results," Journal of Clinical Neuroscience (2003); vol. 10, No. 3, pp. 329-334.
Borgens R B and Bohnert D., "Rapid recovery from spinal cord injury after subcutaneously administered polyetheylene glycol," Journal of Neuroscience Research (2001); vol. 66, pp. 1179-1186.
Ditor D S et al., "Effects of polyethylene glycol and magnesium sulfate administration on cinically relevant neurological outcomes after spinal cord injury in the rat," Journal of Neuroscience Research (2007); vol. 85, pp. 1458-1467.
The International Search Report and the Written Opinion of the International Searching Authority in PCT/US2007/067580.

(Continued)

*Primary Examiner* — Ernst V Arnold
*Assistant Examiner* — Hong Yu
(74) *Attorney, Agent, or Firm* — William D. Schmidt; Sorell, Lenna & Schmidt LLP

(57) ABSTRACT

The invention provides compositions, kits, and methods for treatment of neuronal injury. In one embodiment, the composition comprises a biomembrane sealing agent, such as PEG, and a bioactive agent, such as a magnesium compound. The biomembrane sealing agent and/or the bioactive agent an intravenous administration, an intramuscular administration, an intrathecal administration, a subcutaneous administration, an epidural administration, a parenteral administration, a direct application onto or adjacent to a site of the pathological condition, and any combinations thereof. Alternatively, the biomembrane sealing agent and/or the bioactive agent may be delivered from a pump or an implant.

58 Claims, No Drawings

(56) References Cited

OTHER PUBLICATIONS

Turner, et al., "Magnesium gluconate offers no more protection than magnesium sulphate following diffuse traumatic brain injury in rats.", *Journal of the American College of Nutrition*, 23(5), (2004), 541S-544S.

Muir, et al., "Magnesium for acute stroke (Intravenous Magnesium Efficacy in Stroke trial): randomised controlled trial.", *The Lancet*, 363(9407), (Feb. 7, 2004), 439-45.

Saver, et al., "Prehospital Neuroprotective Therapy for Acute Stroke: Results of the Field Administration of Stroke Therapy-Magnesium (FAST-MAG) Pilot Trial.", *Stroke*, 35(5), (2004), 106-108.

Bittner, et al., "Reconnection of severed nerve axons with polyethylene glycol.", *Brain Research*, 367(1-2), (1986), 351-355.

McIntosh, et al., "Magnesium protects against neurological deficit after brain injury.", *Brain Research*, 482(2), (1989), 252-260.

Shapiro, et al., "Oscillating field stimulation for complete spinal cord injury in humans: a Phase 1 trial.", *J. Neurosurg Spine*, 2(1), (Jan. 2005), 3-10.

Resende, et al., "Local transcutaneous electrical stimulation (TENS) effects in experimental inflammatory edema and pain.", *European Journal of Pharmacology*, 504(1), (2004), 217-222.

Kwon, et al. "Magnesium Chloride in a Polyethylene Glycol Formulation as a Neuroprotective Therapy for Acute Spinal Cord Injury: Preclinical Refinement and Optimization," Journal of Neurotrauma 26, 1379-1393 (Aug. 2009).

Kwon, et al. "A Grading System to Evaluate Objectively the Strength of Pre-Clinical Data of Acute Neuroprotective Therapies for Clinical Translation in Spinal Cord Injury," Journal of Neurotrauma, 28, 1525-1543 (Aug. 2011).

Kwon, et al. "Translational Research in Spinal Cord Injury: A Survey of Opinion from the SCI Community," Journal of Neurotrauma, 27, pp. 21-33 (Jan. 2010).

McKee, et al. "Analysis of the Brain Bioavailability of Peripherally Administered Magnesium Sulfate: A Study in Humans with Acute Brain Injury Undergoing Prolonged Induced Hypermagnesemia," Crit. Care Med., 33(3), 661-666 (Mar. 2005).

Journal of Spinal Cord Medicine, 34(6), 620-621 (2011).

\* cited by examiner

COMPOSITIONS COMPRISING BIOMEMBRANE SEALING AGENT FOR TREATMENT OF NEURONAL INJURY, AND METHODS OF USE

FIELD OF THE INVENTION

This invention relates to methods and composition of treating conditions associated with neuronal injury.

BACKGROUND

Clinical indications affecting the central nervous system such as traumatic brain injury (TBI), spinal cord injury (SCI) and stroke are leading causes of mortality and morbidity in the industrialized world. For example, about 1 million of Americans per year are treated for brain injury in emergency rooms. Approximately 5% of the TBI patients die and 30% of the survivors are generally left with moderate to severe disabilities that may impair their ability to return to work or live independently. Following neuronal injury, a significant proportion of patients will also develop chronic painful conditions.

Pain in general is associated with a myriad of medical conditions and affects millions of Americans. As reported by the American Pain Foundation, over 50 million Americans suffer from chronic pain including 20% of individuals aged 60 and over who are affected by joint disorders such as arthritis. Furthermore, nearly 25 millions Americans experience acute pain due to injuries or surgical procedures each year. In addition to its economical burden, pain has a tremendous effect on the quality of life of affected individuals and is one of the most common causes of disability.

Accordingly, novel improved methods and compositions of treating neuronal injuries are desired to alleviate these debilitating conditions.

SUMMARY OF INVENTION

The instant invention fulfills this and the other foregoing needs by providing novel compositions, kits, and methods for treatment of pathological conditions accompanied by neuronal injury. In one aspect, the present invention provides a pharmaceutical composition comprising at least one biomembrane sealing agent and at least one bioactive agent, wherein the at least one biomembrane sealing agent comprises more than about 10% of the composition. In one embodiment of the invention, the composition is incapable of forming a gel.

In different embodiments of the invention, the at least one biomembrane sealing agent is selected from the group consisting of polyoxyethylenes, polyalkylene glycol, polyethylene glycol or PEG, polyvinyl alcohol, pluronics, poloxamers, methyl cellulose, sodium carboxylmethyl cellulose, hydroxyethyl starch, polyvinyl pyrrolidine, dextrans, poloxamer P-188, and any combinations thereof.

The at least one bioactive agent is selected from the group consisting of at least one magnesium compound, antioxidants, neurotransmitter and receptor modulators, anti-inflammatory agents, anti-apoptotic agents; nootropic and growth agents; modulators of lipid formation and transport; blood flow modulators; electrical stimulation and any combinations thereof.

In other embodiments, the at least one bioactive compound comprises at least one inosine, dexanabinol, electrical or magnetic stimulation, CP 101,606, RPR117824, CD11b/CD18 antibody, CD95 Blocker, ATL-146e, CM101, Riluzole, Topiramate, Amantadine, Gacyclidine, BAY-38-7271, S-1749, YM872, IL-1, IL-8 and TNF-alpha blockers, IL-10, DFU, NXY-059, Edaravone, N-tert-butyl-alpha-phenylnitrone, glutathione and derivates, Rho kinase inhibitors, erythropoietin, steroids, statins IGF-1, GDNF, choline or CDP-choline, creatine, AIT-082, Cyclosporine A, FK-506, Minocycline, Triamcinolone, Methylprednisolone or any combination thereof.

In different embodiments, the at least one magnesium compound comprises magnesium sulfate, magnesium chloride, magnesium gluconate, magnesium ATP, or any combination thereof.

In another aspect, the invention provides a formulation comprising at least one biomembrane sealing agent and at least one bioactive agent.

In yet another aspect, the invention provides a method of treating a pathological condition, selected from the group consisting of a neuronal injury, a tissue injury, a surgical intervention, and any combination thereof, the method comprising delivering to a subject in need thereof a therapeutically effective amount of at least one biomembrane sealing agent and a therapeutically effective amount of at least one bioactive agent, wherein the at least one biomembrane sealing agent is delivered in an injectable composition, wherein the at least one biomembrane sealing agent comprises more than about 10% of the injectable composition. In one embodiment of the invention, the composition is incapable of forming a gel. In different embodiments, the at least one biomembrane sealing agent and the at least one bioactive agent may be delivered by a method selected from the group consisting of an intravenous administration, an intramuscular administration, an intrathecal administration, a subcutaneous administration, an intra-articular administration, an epidural administration, a parenteral administration, a direct application onto a site of the pathological condition, an implanted depot, and any combinations thereof.

DETAILED DESCRIPTION

The instant invention provides novel compositions, kits, and methods for treatment of pathological conditions accompanied by neuronal injury. The discovery of a synergistic effect between PEG, a biomembrane sealing agent, and magnesium is highly significant as it can lead to the development of therapeutic formulations with improved efficacy for the treatment of neuronal trauma.

Definitions

To aid in the understanding of the invention, the following non-limiting definitions are provided:

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

The term "subject" includes a living or cultured system upon which the methods and/or kits of the current invention is used. The term includes, without limitation, humans.

The term "practitioner" means a person who practices methods, kits, and compositions of the instant invention on the subject. The term includes, without limitations, doctors, other medical personnel, and researchers.

The terms "neuropathic pain" and "neural origin pain" refer to pain initiated or caused by a pathological condition of the nervous system, including, without limitation, pathology following chronic or acute insults.

The hallmarks of neuropathic pain are chronic allodynia and hyperalgesia. Accordingly, the term "allodynia" refers to pain resulting from a stimulus that ordinarily does not elicit a painful response.

The term "hyperalgesia" refers to an increased sensitivity to a normally painful stimulus. Primary hyperalgesia affects the immediate area of the injury.

The term "secondary hyperalgesia" or "referred pain" is normally utilized in cases when sensitization has extended to a broader area surrounding the injury.

The term "neuronal injury" refers to an insult to an element of the central or peripheral nervous systems. Neuronal injuries can be derived from a physical (including mechanical, electrical or thermal), ischemic, hemorrhagic, chemical, biological or biochemical insult. Examples of neuronal injuries include, without limitations, ischemic and hemorrhagic stroke, spinal cord, brain, cranial nerve and peripheral nerve injuries.

The term "bioactive agent" refers to molecules and physical stimuli.

All references to chemical compounds, including without limitation, bioactive agents, biomembrane sealing agents, and markers, include all forms of these chemical compounds (i.e., salts, esters, hydrates, ethanolates, etc.), wherein said forms possess at least partial activities of the respective chemical compounds.

There are two basic forms of physical pain: acute and chronic. Acute pain, for the most part, results from disease, inflammation, or injury to tissues. It is mediated by activation of sensory fibers also known as nociceptive neurons. Nociceptive pain normally disappears after healing, for example in cases of post-traumatic or post-operative pain. Unfortunately, in some individuals, pathological changes occur that increase the sensitivity of the sensory neurons. In those cases, symptomatic pain can become chronic and persists for months or even years after the initial insult.

Neuronal injuries are complex clinical conditions aggravated by a variety of precipitating causes that influence the severity of injury and ultimately influence the course and extent of recovery. A primary insult to a component of the central and/or peripheral nervous system could be of mechanical, chemical, biological or electrical nature. Following the primary insult, a cascade of biochemical and physiological events takes place that often leads to pathobiological changes that are considered largely responsible for the development of irreversible damages. This autodestructive cascade is known as secondary injury and because it develops over time after the traumatic event it opens a window of opportunity for pharmacological interventions. Various chronic conditions linked to persistent on-going tissue damage due, for example, to inflammatory reactions or autoimmune diseases, may also lead to secondary injury of neuronal components and symptomatic pain.

There are at least three major classes of events that are determinant in the secondary phase of the traumatic brain injury (TBI) pathology and other neuronal injuries. One of these is membrane damages to cells that managed to survive the first impact. Small changes in membrane integrity and/or cytoskeletal architecture can impair membrane potential, intracellular transport and ATP production leading to cytoskeletal collapse, mitochondrial dysfunction, energetic failure and free radical production resulting in cell death by either apoptotic or necrotic mechanisms. In some instances, the dying cells can release free radicals and catabolic enzymes (proteinase, peptidases, caspases) that may cause damages to the surrounding cells and increase the number of injured cells. Unfortunately, neuronal cells are particularly vulnerable to membrane damages due to their high energetic demand and their unique anatomical structure which increase by many folds the challenge of maintaining efficient membrane integrity and intracellular (axonal) transport.

The other class of events that plays a major role in the secondary phase of neuronal injuries is the storm of neurotransmitter release which by mechanisms globally referred as "excitotoxicity" can increase the vulnerability of neurons to any additional insults in an area that, in size, extend far beyond the area directly affected by the first insult. For example, a marked increase in extracellular glutamate levels is often associated with neuronal insults. Since glutamate is the most prominent excitatory neurotransmitter of the central nervous system, almost all neurons have glutamate receptors and will be affected by the toxic events triggered by excessive amounts of extracellular glutamate. Excitotoxicity insults are thought to be largely triggered by excessive inflow of $Ca^{2+}$ through a specific subtype of glutamate receptor, the N-methyl-D-aspartate receptors (NMDAR). High concentrations of intracellular $Ca^{2+}$ can activate catabolic enzymes and production of free radicals that may interfere with the repair mechanisms of the cell or its ability to cope with additional challenges or even precipitate cell death.

The third class of detrimental events is linked to vascular damages and breakdown of the blood-brain barrier. In animal models of TBI and SCI, the blood-brain barrier remains disrupted for many days after injury (Schnell et al., 1999) allowing for extravasation of plasma proteins and invasion of the central nervous system (CNS) by blood and immune cells.

Although the role of inflammation in brain injury and other forms of neuronal injuries remains controversial, proper distribution of nutrients to the nervous tissue cannot be accomplished before the blood-brain barrier and the cerebral vessels are repaired.

Inflammation is the body's normal protective response to conditions that include a tissue necrosis component. Tissue necrosis can be derived from a physical (including mechanical, electrical or thermal), chemical, biological or biochemical insult. Clinical conditions with an inflammatory component include traumatic tissue injury, surgery, degenerative diseases such as arthritis and other joint diseases as well as irritation, hypersensitivity, and auto-immune reactions.

During this natural "defense" process, local increases in blood flow and capillary permeability lead to accumulation of fluid, proteins and immune cells in the inflamed area. Some of these cells can release chemical mediators of inflammation including histamine, cytokines, bradykinin and prostaglandins that can attract more immune cells at the site of inflammation and/or increase the sensitivity of pain fibers within the affected area. As the body mounts this protective response, the symptoms of inflammation develop. These symptoms include, without limitation, pain, swelling and increased warmth and redness of the skin. The inflammatory response has to be tightly regulated otherwise it may lead to tissue necrosis and development of chronic pain.

Biomembrane Sealing Agents

For more than 40 years, biomembrane sealing agents of various molecular weights have been utilized as adjuncts to culture media for their ability to protect cells against fluid-mechanical injuries. These agents include hydrophilic polymers such as polyoxyethylenes, polyethylene glycols (PEG), polyvinyl alcohol, amphipatic polymers such as pluronics or poloxamers, including poloxamer P-188 (also known as CRL-5861, available from CytRx Corp., Los Angeles, Calif.) (Michaels and Papoutsakis, 1991) as well as methyl cellulose (Kuchler et al., 1960), sodium carboxylmethyl cellulose, hydroxyethyl starch, polyvinyl pyrrolidine and dextrans (Mizrahi and Moore, 1970; Mizrahi, 1975; Mizrahi, 1983).

Some biomembrane sealing agents including hydroxyethyl starch (Badet et al., 2005) and PEG (Faure et al, 2002; Hauet et al., 2001) have shown effective cryopreservative abilities in organ transplantation studies. Poloxamer P-188 was shown to protect articular cells from secondary injury following mechanical trauma to knee joint which could lead to acute pain and inflammation and potentially develop into a more chronic condition known as osteoarthritis (Phillips and Haut, 2004). Poloxamer P-188 and a neutral dextran protected muscle cells against electroporation or thermally driven cell membrane permeabilization (Lee et al., 1992). Direct application of PEG was shown to anatomically and functionally reconnect transected or crushed axon (Bittner et al., 1986), peripheral nerve (Donaldson et al., 2002) and spinal cord preparations in vitro (Lore et al., 1999; Shi et al., 1999; Shi and Borgens, 1999; Shi and Borgens, 2000; Luo et al., 2002) or in vivo (Borgens et al., 2002). Intravenous or subcutaneous administration of PEG or Poloxamer P-188 improved the cutaneous trunchi muscle reflex response after experimental spinal cord contusion in guinea pigs (Borgens and Bohnert, 2001; Borgens et al., 2004) and improved functional recovery in a naturally occurring spinal cord injury model in dogs (Laverty et al., 2004). PEGs of various molecular weights from 1,400-20000 Da, having a linear or multiple arms structure were shown to improve recovery following tissue injury (Hauet et al., 2001; Detloff et al., 2005; Shi et al., 1999).

Biomembrane sealing agents can be effective following different modes of delivery including local and prolonged cellular exposure, direct and short-term tissue or organ exposure or systemic administration. Effective concentrations of biomembrane fusion agents may vary depending on the purpose and/or mode of delivery For example, about 0.05% concentration is effective in tissue culture applications (Michaels and Papoutsakis, 1991) and about 30% to about 50% concentration is effective for organ preservation and upon in vivo administration in animals (Hauet et al., 2001; Shi et al., 1999; Borgens and Bohnert, 2001; Borgens et al., 2004).

Bioactive Agents

As discussed above, inventors have found that a combination of a biomembrane sealing agent and a magnesium compound is useful for the treatment of neuronal trauma and painful conditions. Accordingly, in one embodiment of the invention, the at least one bioactive agent comprises a magnesium compound. Magnesium plays an important role in a large diversity of cellular functions. For example, magnesium is required for glycolysis and oxidative phosphorylation which support energy-producing and energy-consuming reactions in cells. Protein synthesis as well as membrane structure and function are also magnesium-dependent. Levels of magnesium will affect neurotransmitter release including glutamate and acetylcholine release. It also regulates the activity of calcium transporters and opening of the non-methyl-D-aspartate (NMDA) glutamate receptors. Magnesium is known to have anti-oxidant, anti-apoptosis and to modulate lipid formation and transport. In addition to its cellular effects, magnesium can modulate physiological functions involved in regulation of blood flow and edema development.

During the last decade, a number of studies have reported that brain levels of free magnesium decline following TBI in animal model and in clinical settings. Decrease in brain levels of free magnesium from 40 to 60% has been observed in various TBI animal models including the fluid percussion model (Vink et al., 1991; Headrick et al., 1994), focal impact model (Suzuki et al., 1997) as well as more diffuse models of brain injury (Heath and Vink, 1996; Smith et al., 1998). Furthermore, in the rodent fluid percussion TBI model, a linear correlation was established between changes in brain free magnesium levels, energetic potential (phosphorylation potential) and functional (motor) outcomes (reviewed in Vink and Cernak, 2000). Decreases in magnesium levels have also been reported in experimental spinal cord injury (Vink et al., 1989).

A direct correlation was also established in TBI patients between levels of magnesium and the level of recovery (Mendez et al., 2005). TBI patients as well as human suffering from acute ischemic and/or cerebrovascular events are more susceptible to develop a condition called hypomagnesemia where availability of free magnesium is impaired (Polderman et al., 2000). Hypomagnesemia is also associated with increased mortality in patients in general who require the attention of the intensive care unit (Chernow et al., 1989; Rubeiz et al., 1993).

Magnesium supplementation initiated from minutes to hours after onset of CNS trauma showed neuroprotective effects in animal models of TBI (Heath and Vink, 1999; Esen et al., 2003; Vink et al., 2003; Feng et al., 2004 and Turner et al., 2004), spinal cord injury (Suzer et al., 1999; Kaptanoglu et al., 2003) and stroke (Yang et al., 2000; Westermaier et al., 2003 and 2005).

Clinical evaluation of intravenous administration of magnesium sulfate up to 12 hours following stroke onset showed no significant improvement in a multicenter trial involving 2589 patients (Muir et al., 2004). A follow-up study has been initiated to look at the potential effect of an earlier intervention where magnesium sulfate would be administered within 2 hours of stroke onset (Saver et al., 2004). Another clinical trial initiated in 1999 at the University of Washington (Seattle) was evaluating magnesium sulfate therapy for TBI patients and preliminary data were also negative in this trial.

Magnesium supplementation has also been extensively studied in animals and humans for its ability to reduce acute and chronic pain. However, mixed results have been reported from clinical trials evaluating the efficacy of magnesium (alone or in combination) in reducing pain associated with various surgical procedures (Bolcal et al., 2005; Apan et al., 2004; Bathia et al., 2004; McCartney et al., 2004), headache and acute migraine attacks (Cete et al., 2005; Corbo et al., 2001; Bigal et al., 2002), peripheral neuropathies (Brill et al., 2002; Felsby et al., 1996), cancer (Crosby et al., 2000), primary fibromyalgia syndrome (Moulin, 2001; Russel et al., 1995) and chronic limb pain (Tramer and Glynn, 2002). In addition, it appears that magnesium analgesic effect may be of a short duration such as 4 hours or less (Crosby et al., 2000). Magnesium may also induce side effects such as flushing and aching that can reduce its therapeutic window (Tramer and Glynn, 2002). Magnesium supplementation therapies can be achieved by using various salts including magnesium sulfate, chloride, gluconate and magnesium-ATP leading to similar neuroprotective effects in animal models of CNS injury (McIntosh et al., 1989; Izumi et al., 1991; Hoane et al., 2003; Turner et al., 2004; reviewed in Vink and McIntosh, 1990).

The inventors have found that administration of PEG alone or magnesium alone had no effect on the loss of cognitive functions following brain injury whereas cognitive functions or more precisely, the ability to learn a new spatial task, was improved by >30% in animals treated with both PEG and magnesium solutions. Combined treatment with PEG and magnesium was also significantly more potent than treatment with either component alone in animal models of SCI reducing the lesion size by half, improving locomotor recovery and reducing the occurrence of neuropathic pain. In an acute model of tissue inflammation, the combined PEG and magnesium solution was also more effective than PEG or magnesium alone at reducing symptomatic pain. The discovery of a synergistic effect between PEG, a biomembrane sealing agent, and magnesium is highly significant as it can lead to the development of therapeutic formulations with improved efficacy for the treatment of neuronal trauma, inflammatory and painful conditions.

These results suggest that a biomembrane sealing agent, such as, for example, PEG, may also potentiate the beneficial effects of other therapeutic agents. In different embodiments, such bioactive agents include, neurotransmitter and receptor modulators, anti-inflammatory agents, antioxidants, anti-apoptotic agents, nootropic and growth agents; modulators of lipid formation and transport, electrical stimulation, blood flow modulators and any combinations thereof.

Suitable examples of antioxidants include, without limitation, free radical scavengers and chelators enzymes, co-enzymes, spin-trap agents, ion and metal chelators, lipid peroxidation inhibitors such as flavinoids, N-tert-butyl-alpha-phenylnitrone, NXY-059, Edaravone, glutathione and derivates, and any combinations thereof.

Suitable examples of anti-inflammatory agents, include, without limitation, steroids such as methyl prednisolone, Triamcinolone, modulators of an inflammatory cytokine such as IL-10, IL-1, IL-8, TNF-alpha and their receptors, COX inhibitor such as DFU and modulators of immune cell functions such as CD11b/CD18 antibody.

Suitable examples of neurotransmitter and receptor modulators include, without limitations, glutamate receptor modulators, cannabinoid receptors modulators, and any combinations thereof. A person of ordinary skill in the art will appreciate that one of the receptor modulators is a ligand naturally occurring in a subject's body. For example, glutamate receptors modulators include glutamate.

In another embodiment, the at least one bioactive agent is a modulator of glutamate transmission, such as (1S, 2S)-1-(4-hydroxyphenyl)-2-(4-hydroxy-4-phenylpiperidino)-1-propanol (also known as CP-101,606), Riluzole (Rilutek®), Topiramate, Amantadine, Gacyclidine, BAY-38-7271, S-1749, YM872 and RPR117824.

In another embodiment, the at least one bioactive agent is a cannabinoid receptor modulator such as dexanabinol (Pharmos Corporation, Iselin, N.J., USA).

Anti-apoptotic agents include, without limitations, inhibitors of pro-apoptotic signals (e.g., caspases, proteases, kinases, death receptors such as CD-095, modulators of cytochrome C release, inhibitors of mitochondrial pore opening and swelling); modulators of cell cycle; anti-apoptotoc compounds (e.g., bcl-2); immunophilins including cyclosporine A, minocycline and Rho kinase modulators, and any combinations thereof. Suitable non-limiting examples of Rho pathway modulators include Cethrin, which is a modified bacterial C3 exoenzyme (available from BioAxone Therapeutics, Inc., Saint-Lauren, Quebec, Canada) and hexahydro-1-(5-isoquinolinylsulfonyl)-1H-1,4-diasepine (also known as Fasudil, available from Asahi Kasei Corp., Tokio, Japan).

Nootropic and growth agents include, without limitation, growth factors; inosine, creatine, choline, CDP-choline, IGF, GDNF, AIT-082, erythropoietin, Fujimycin (IUPAC name [3S-[3R*[E(1S*,3S*,4S*)],4S*,5R*, 8S*,9E,12R*,14R*, 15S*,16R*,18S*,19S*,26aR*]]-5,6,8,11,12,13,14,15,16,17, 18,19,24,25,26,26a-hexadecahydro-5,19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-c][1,4]oxaazacyclotricosine-1,7,20,21 (4H,23H)-tetrone, monohydrate, also known as FK-506 and any combinations thereof.

Suitable non-limiting examples of modulators of lipid formation, storage, and release pathways are apolipoprotein; statins; and any combinations thereof.

Suitable non-limiting of blood flow modulators are adenosine receptor modulators such as ATL-146e and agents that modulate new vessel formation such as CM101.

In yet another embodiment, the at least one bioactive agent is an electrical or magnetic stimulation. Electrical or magnetic stimulation may be delivered from a site adjacent to the site of a pathological condition (e.g., trauma). For example, if the pathological condition is a spinal injury at the level of C-6, the electrical or magnetic stimulation may be delivered one segment above and one segment below the trauma (i.e., C-5 and C-7).

A person of ordinary skill in the art will appreciate that multiple sources exist for delivering the electrical or magnetic stimulation. In one embodiment, the source is an Oscillating Field Stimulator (OFS) as described, for example in Shapiro, *J. Neurosurg. Spine*, 2:3-10 (2005), incorporated herein by reference in its entirety. Briefly, the outside case of the OFS can be made of materials known to be safe for human applications, such as, for example, a fluoropolymer and a silicone sealant. Inside the case are the power block, timing/switching block, current regulation block, and fail-safe device. The power block provides the direct-current power source for the unit involving a single 3.6-V organic lithium battery with a rated capacity of 2400 mAmp/hour. The timing/switching block includes a complementary metal oxide semiconductor 14-stage binary ripple counter device with an onboard oscillator timed for 15-minute intervals along with a single-pole double-throw analog switch. A fail-safe semiconductor chip is programmed to shut down the OFS if the power falls to 2.6 V, if there is a failure to oscillate, or if there are current changes indicative of an internal short circuit. Current regulation can be set by another semiconductor device that delivers 200 µAmp to each pair of electrodes for a total current of 600 µAmp. The electrodes can be made of standard pacemaker cable and a platinum/iridium tip with a 4.72-mm$^2$ surface area. A magnet-controlled reed switch can be used to turn the device on or off. When a magnet is on the switch, the device is turned off. When the unit is turned on, it delivers a field of 500 to 600 µV/mm and a current density of 42.4 µAmp/mm$^2$ for each electrode.

Thus, in one embodiment of the invention the total current of electrical or magnetic stimulation may be between about 400 µAmp and about 700 µAmp, or between about 450 µAmp and about 650 µAmp, or between about 500 µAmp and about 600 µAmp. The current density of the electrical or magnetic stimulation may be between about 30 µAmp/mm$^2$ and about 50 µAmp/mm$^2$, between about 40 µAmp/mm$^2$ and about 45 µAmp/mm$^2$, or about 43 µAmp/mm$^2$.

In another embodiment, a transcutaneous electrical nerve stimulation (TENS) may be used as the at least one bioactive agent. A person of ordinary skill in the art will appreciate that one advantage of TENS is that it is non-invasive and that the guidelines for TENS are provided, for example, in Resende et al., *Eur. J. Pharmacol.* 504:217-222 (2004), incorporated herein by reference in its entirety. Conveniently, the practitioner may use equipment which is commercially available, such as, for example, a Neurodyn III apparatus (IBRAMED, Brazil).

If TENS is selected as the at least one bioactive agent of choice, in different embodiments of the invention, the electrical stimuli may be released with a frequency of between about 4 Hz and about 130 Hz, wherein a duration of an individual electrical stimulus is between about 60 and about 200 µs, or between about 100 and about 160 µs or between about 125 and 135 µs.

Thus, a combined treatment comprising an administration of a biomembrane sealing agent, such as for example, one of the polymers disclosed above, and at least one bioactive agent, such as, for example, a magnesium compound, has a positive and synergistic effect in reducing the lesion size, improving functional recovery and reducing chronic pain following neuronal trauma as well as reducing acute pain linked to tissue inflammation.

Accordingly, in one aspect, the invention comprises a pharmaceutical composition comprising at least one biomembrane sealing agent and at least one bioactive agent, wherein the at least biomembrane sealing agent comprises more than about 10% of the composition. In one embodiment of the invention, the composition is incapable of forming a gel. As discussed above, in one embodiment, the at least one active agent comprises at least one magnesium compound.

A person of ordinary skill in the art will undoubtedly recognize that at least one magnesium compound may be just about any molecule providing a source of magnesium ions, such as, for example, a magnesium salt. In a preferred embodiment, the magnesium salt is non-toxic. Suitable non-limiting examples of the at least one magnesium compound include magnesium sulfate, magnesium chloride, magnesium gluconate, magnesium ATP, and any combination thereof.

A person of ordinary skill in the art will also appreciate that at least one marker may be included into the pharmaceutical composition of the present invention. For example, the at least one marker may comprise any molecule or a cocktail of ingredients distribution of which is easy to visualize and monitor. Thus, in one embodiment, the at least one marker may be a radiographic marker, such as for example, barium, calcium phosphate, and metal beads. In another embodiment, the at least one marker may comprise iodine-based contrast agents, such as, for example, iopamidol, commercially available as Isovue™ (Bracco Diagnostics Inc., Princeton, N.J.) or iodixanol, commercially available as Visipaque™ (Nyocomed, Inc., Princeton, N.J.), and gandolinium-based contrast agents, such as, for example, gadodiaminde, commercially available as Omniscan™ (available from GE Healthcare, Princeton, N.J.).

Therapeutic Formulations

Therapeutic formulations comprising the pharmaceutical composition of the present invention can be prepared for storage by mixing the at least one biomembrane sealing agent and the at least one bioactive agent with optional physiologically acceptable carriers, excipients or stabilizers (see, e.g., Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenyl, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; and/or metal complexes (e.g., Zn-protein complexes).

The formulations herein may also contain more than one active compound as necessary for the particular indication being treated, preferably those with complementary activities that do not adversely affect each other. Such molecules are suitably present in combination in amounts that are effective for the purpose intended.

The at least one bioactive agent and/or the at least one biomembrane sealing agent may also be entrapped in a microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may also be prepared. Suitable examples of sustained-release preparations include semipermeable matrices of solid polymers containing the at least one biomembrane sealing agent and/or the at least one bioactive agent, which matrices are in the form of shaped articles, e.g., films, or microcapsule. Examples of sustained-release matrices include, without limitations, polyesters, hydrogels (for example, poly(2-hydroxyethyl-methacrylate), or poly(vinylalcohol)), polylactides (see, e.g., U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. Polymers such as ethylene-vinyl acetate and lactic acid-glycolic acid enable release of molecules for over 100 days.

A person of ordinary skill in the art will undoubtedly appreciate that the at least one biomembrane sealing agent may be included into or used as the semipermeable matrix. In this embodiment, both the at least one biomembrane sealing agent and the at least one bioactive agent are released as the semipermeable matrix degrades.

Further, a person of ordinary skill in the art will recognize that the at least one biomembrane sealing agent and/or the at least one bioactive agent may be implanted into the subject, for example, in forms of a pump or a depot. A suitable non-limiting design of a depot implant is discussed in details in a co-pending application Ser. No. 11/403,373 entitled Drug Depot Implant Designs And Methods Of Implantation, filed on Apr. 13, 2006.

A person of ordinary skill in the art will recognize that the use of the at least one marker is especially advantageous in combination with this embodiment of the invention. The at least one marker may be included on the drug depot implant itself. In this embodiment, a practitioner will be better equipped to accurately position the implant into a tissue of a patient. As discussed above, the at least one marker may be a radiographic marker, such as, for example, barium, calcium phosphate, and metal beads. In another embodiment, the at least one marker may comprise iodine-based contrast agents, such as, for example, iopamidol, commercially available as Isovue™ (Bracco Diagnostics Inc., Princeton, N.J.) or iodixanol, commercially available as Visipaque™ (Nyocomed, Inc., Princeton, N.J.), and gandolinium-based contrast agents, such as, for example, gadodiaminde, commercially available as Omniscan (available from GE Healthcare, Princeton, N.J.). Such markers will also permit the practitioner to track movement and degradation of the implant in the tissue over time. In this embodiment of the invention the practitioner may accurately position the implant in the tissue using any of the numerous diagnostic imaging procedures known to one of ordinary skill in the art. Such diagnostic imaging procedures include for example, X-ray imaging or fluoroscopy.

In another embodiment, the at least one biomembrane sealing agent and/or the at least one bioactive agent may be administered locally via a catheter positioned at or near a site of the pathological condition, e.g., neuronal injury. In this embodiment, the catheter has a proximal end and a distal end, the proximal end having an opening to deliver the at least one biomembrane sealing agent and/or the at least one bioactive agent in situ, the distal end being fluidly connected to a pharmaceutical delivery pump. For example, the proximal end of the catheter delivers the at least one biomembrane sealing agent and/or the at least one bioactive agent within 10 cm of the site of the pathological condition, more particularly, within 5 cm of the site of the pathological condition, and even more particularly, within 1 cm of the site of the pathological condition. The catheter may be positioned via a minimally invasive procedure, such as, for example, by accessing a blood vessel adjacent or supplying blood to the site of the pathological condition.

It would be within the expertise of a person of ordinary skill in the art to recognize that the at least one biomembrane sealing agent and the at least one bioactive agent may be delivered independently of each other. In one non-limiting example, the at least one biomembrane sealing agent may be delivered through an intramuscular injection and the at least one bioactive agent is delivered via an implant. A person of ordinary skill in the art will undoubtedly recognize that a large number of combinations is possible.

A person of ordinary skill in the art will further recognize that in some cases it may be advantageous to ship and store the at least one biomembrane sealing agent and the at least one bioactive agent separately and pre-mix these compounds at a desired time, e.g., one hour prior to administration, or even to administer those compounds without pre-mixing. Accordingly, in another aspect, the invention provides a kit comprising at least one biomembrane sealing agent, at least one bioactive agent and a set of instructions comprising information on making an injectable composition, wherein the at least one biomembrane sealing agent comprises more than about 10% of the composition. In one embodiment of the invention, the composition is incapable of forming a gel.

A person of ordinary skill in the art will further recognize that the kit provides a practitioner with an advantageous flexibility in selecting the ratios of the at least one biomembrane agent and the at least one bioactive agent.

A person of ordinary skill in the art will also appreciate that the set of instruction may be provided in any medium, including, without limitations, printed, audio and video recorded, and electronic.

In another aspect, the invention provides a method of treating a pathological condition, selected from the group consisting of a neuronal injury, a tissue injury, a surgical intervention, and any combination thereof, the method comprising delivering to a subject in need thereof a therapeutically effective amount of at least one biomembrane sealing agent and a therapeutically effective amount of at least one bioactive agent, wherein the at least one biomembrane sealing agent is delivered in an injectable composition, wherein the at least one biomembrane sealing agent comprises more than about 10% of the injectable composition. In one embodiment of the invention, the composition is incapable of forming a gel. In different embodiments, the pathological condition is selected from the group consisting of neuronal injury, tissue injury, inflammation, and any combination thereof.

Examples of suitable pathological conditions include, without limitations, metabolic neuropathies such as diabetic and alcoholic neuropathies, posttherapeutic neuralgia, trauma to the central nervous system such as stroke, traumatic brain, spinal cord or cauda equine injuries, pain derived from mechanical or biochemical neuronal insults such as carpal tunnel syndrome, phantom limb pain and symptomatic pain associated with degenerative conditions such as multiple sclerosis, arthritis and other joint diseases, persistent symptomatic pain derived from surgical or other invasive interventions as well as chronic pain derived from injury of peripheral neuronal or non-neuronal tissues.

The therapeutically effective amount of at least one biomembrane sealing agent and the therapeutically effective amount of at least one bioactive agent may be delivered independently of each other by an intravenous administration, an intramuscular administration, intrathecal administration, subcutaneous administration, epidural administration, intra-articular administration, parenteral administration, direct application onto or adjacent to a site of the pathological condition, and any combinations thereof. Initiation of individual treatments could be separated by a few hours, e.g., up to about 24 hours, or more preferably, up to about 16 hours, or more preferably of up to about 8 hours, or even more preferably, up to 4 hours. Thus, the at least one biomembrane sealing agent and the at least one bioactive agent may be delivered from independent sources and/or by different methods, or they may be mixed prior to delivery.

A person of ordinary skill in the art will further recognize that certain invasive procedures, such as, for example, brain or spinal cord surgeries, leave a subject with a neuronal injury. Accordingly, in one embodiment of the invention, the at least one biomembrane sealing agent and/or the at least one bioactive agent is delivered to the subject prior to the event triggering the occurrence of the pathological condition. In one non-limiting example, the event is brain surgery and the pathological condition is an injury to CNS neurons.

Specific embodiments according to the methods of the present invention will now be described in the following non-limiting examples.

EXAMPLES

Example 1

Treatment with a Combination of PEG and Magnesium Compound but not with PEG Alone or with Magnesium Compound Alone Improved Cognitive Functions Following TBI Animals Male Sprague-Dawley rats (Harlan Sprague-Dawley, Indianapolis, Ind.), weighing 350-450 grams each were given free access to food and water before the experiment. The animals were anesthetized with halothane (1% in 70%/30% $NO_2/O_2$ by mask).

Brain temperatures were monitored using a rectal thermometer. The animals' body temperature was maintained at 37° C. by using a water-jacketed heating pad. Brain temperature was monitored for 1 hour prior to injury to 6 hours following injury and was recorded at 30-minute intervals.

The controlled cortical impact model of brain injury utilized in this study has been described in detail (Scheff and Sullivan, 1999). Animals were anesthetized with isoflorane and placed in a stereotaxic frame in the supine position. A 6 mm craniotomy located approximately midway between bregma and lambda, just above the somatosensory cortex, was made using a Michele trephine. The skull disk was then removed without disturbing the underlying dura mater. The exposed brain was injured using an electronically controlled piston (5 mm diameter, 65 kdynes). The animals in the "sham" group underwent identical surgical procedures, but the surface of the brain was not impacted.

Following surgery, animals were placed in their home cage and dosing was initiated. Animals were treated with saline (Group 1: sham, Group 2: injured), PEG (Group 3: injured), magnesium (Group 4: injured) or a combination of PEG and magnesium solutions (Group 5: injured). The PEG solution was composed of PEG3350 at 30% in 0.5% saline (custom made by AAIPharma Developmental Services, Wilmington, N.C.). The magnesium solution was composed of magnesium sulfate at 50% in an injectable formulation (American Regent Laboratories, inc). The magnesium solution was diluted in saline 1:1 before intravenous injection as recommended by the manufacturer. In the cases of combined PEG+Mg combined treatments, animal received the PEG and magnesium components from two individual solutions.

In more details, each animal received 2 injections:
Group 1: Sham—1.23 ml/kg of saline solution followed by 1.23 ml/kg of saline solution;
Group 2: Injured—1.23 ml/kg of saline solution followed by 1.23 ml/kg of saline solution;
Group 3: Injured—2.33 ml/kg of PEG solution followed by 0.12 ml/kg of saline solution;
Group 4: Injured—0.12 ml/kg of magnesium solution followed by 2.33 ml/kg of saline solution;
Group 5: Injured—2.33 ml/kg of PEG solution followed by 0.12 ml/kg of magnesium solution.

The first two injections were administered 15 minutes following injury. Another round of two injections was given 6 hours later. The single doses of PEG and magnesium sulfate administered were of 0.7 g/kg and 0.115 mmol/kg and total dose of 1.4 g/kg and 0.230 mmol/kg (body weight) respectively. The compounds tested were administered by bolus intravenous injection. There were 10 animals per group. These studies were performed in a randomized and blinded fashion such as the solutions were sent to the Research Center in blindly labeled packages and the code was not revealed to the Research Center before the end of the study.

Assessment of Cognitive Function

The effects of PEG, magnesium sulfate and combined treatment on recovery of cognitive function following TBI were evaluated using the Morris Water Maze Test. This behavioral endpoint measure the ability of the rat to learn a new task based on the memorization of spatial cues. It is the most widely utilized behavioral test to assess functional recovery following TBI in rats. Briefly, the open-field circular pool was of 127 cm in diameter×56 cm in height, with a removable circular plastic platform 13.5 cm in diameter (Morris, 1984). The pool and platform were painted flat black in color, and the water was colored black with non-toxic black powdered paint to obscure the platform location. Platform location during training trials was always in the South-East quadrant, approximately 30 cm from the pool wall, and 1 cm below the surface of the water (19-21° C.). Spatial cues located in the testing room remained constant throughout testing. Each day of testing consisted of four 60-s trials to navigate to the hidden platform. Once the platform was located, animals were allowed a 15-s platform sit followed by a 5-min inter-trial interval (ITI). If at the end of 60 s the rat was unable to find the platform, the subject was guided to the platform and allowed a 15-s platform sit, followed by a 5-min ITI. Entry into the water maze was randomized between one of four locations (North, South, East, West) for the training tests each day. Five minutes following the fourth acquisition trial on the fifth day, the platform was removed from the pool and a 30-s probe trial was performed; pool entry during the probe trial was always from the NW location. A video camera (Sony, CCTV Camera) was located directly above the pool to record swimming during training and probe tests. The animals were tested from Day 9-14 following injury and treatment.

To evaluate the significance of difference between experimental groups, data were analyzed using an unpaired, two-tailed t statistical test with confidence intervals of 95%.

The rats in the TBI groups were subjected to anesthesia, craniotomy and controlled cortical impact delivered directly on the dura. The "sham" group underwent identical surgical procedures, but the surface of the brain was not impacted. Following brain injury, the rats were treated with intravenous injections of saline, PEG, Magnesium or combined PEG and Magnesium solutions. All rats received two injection regiments, one fifteen minutes post-injury and another one 6 hours later. From day 9 to day 14 post-injury, the animals were tested for their ability to learn a new task by using the Morris Water Maze. Briefly, the animal is evaluated for its ability to find a hidden platform in a circular pool by using visual cues located on the 4 walls surrounding the pool. Each testing day (day 9-14), the animals are allowed 4 training trials followed by a probe trial. The time required to locate the platform or latency (sec) during the probe trial is reported here.

Following craniotomy only (sham group) or craniotomy and controlled cortical impact (TBI groups), rats were treated with intravenous injections of saline, PEG or Magnesium (Mg) solutions. Treatment with PEG alone or Magnesium alone had no effect on cognitive functions following TBI. Combined PEG and Magnesium (Mg) treatments significantly improved recovery of cognitive functions between days 12-14 post-TBI, reducing the time to locate the platform by approximately 30% relative to animals treated with saline only ($p<0.05$). At day 14 post-injury, combined PEG+Mg treatments also showed a positive and synergistic effect relative to PEG alone treatment ($p<0.0001$) or Mg alone treatment ($p=0.0001$).

Example 2

Treatment with a Combination of PEG and Various Magnesium Compounds are Equally Effective in a Model of TBI Following the same experimental procedure presented in example 1, TBI animals were treated with saline, PEG, magnesium chloride or PEG+magnesium chloride. TBI animals received 2 injections, one injection 15 minutes post-TBI and the second injection 6 hours later. The total doses were 1.4 g/kg PEG and 0.230 mmol/kg magnesium chloride.

Treatment with PEG or magnesium chloride had no significant effect on cognitive recovery after TBI. Combined PEG+magnesium chloride treatments significantly improved recovery of cognitive functions between days 10-14 post-TBI, reducing the time to locate the platform by approximately 30% (as seen for PEG+magnesium sulfate in example 1) relative to animals treated with saline only (p<0.01).

Example 3

Treatment with a Combination of Magnesium and PEG, where PEG is Used at Concentrations from 15-30% are Effective in a Model of TBI Following the same experimental procedure presented in example 1, TBI animals were treated with saline, PEG 15%+ Magnesium chloride, PEG 20%+Magnesium chloride, PEG 30%+Magnesium chloride. TBI animals received 2 injections of 3.33 ml/kg, one injection 15 minutes post-TBI and the second injection 6 hours later. For all 3 solutions, the total dose of magnesium chloride was 0.230 mmol/kg.

In this TBI study, cortical lesion volume was also assessed. Tissue sections were stained with Cresyl Violet and the volume of the cortical lesion will be determined. Twelve equally spaced sections (1 mm) were evaluated using a video-based image analysis system (NIH Image). The lesion volume in each section were determined with a computer-assisted image analysis system, consisting of a Power Macintosh computer equipped with a Quick Capture frame grabber card, Hitachi CCD camera mounted on an Olympus microscope and camera stand. NIH Image Analysis Software, v. 1.55 was used. The images were captured and the total area of damage determined over the twelve sections. A single operator blinded to treatment status performed all measurements. The total cortical area was measured on the ipsilateral side of the brain using lamina 1 and the corpus callosum as boundaries. The area of the cavity produced by the lesion was also calculated for each tissue section. Lesion volume was calculated by multiplying the total length of the cortex analyzed by the average volume of the cortex.

Treatment with combined solutions containing magnesium chloride and PEG at 15, 20 and 30% improved recovery of cognitive functions between days 10-14 post-TBI, reducing the time to locate the platform by approximately 19, 32 and 56%, respectively after TBI.

In addition, treatment with combined solutions containing magnesium chloride and PEG at 15, 20 and 30% reduced the lesion volume by 6, 29 and 47%.

Example 4

Treatment with a Combination of PEG and Magnesium Compound but not with PEG Alone or with Magnesium Compound Alone Improved Motor Functions Following SCI in a Dural Impact Model Animals Sprague-Dawley female rats (200-225 gm) received a spinal cord contusion using the Precision Scientific Inc pneumatic impactor. Prior to surgery, rats were assigned to different treatment groups based on a randomized block design so that on any given surgery day all treatments would be included. The rats were anesthetized with ketamine (80 mg/kg) and xylazine (10 mg/kg) before a laminectomy will be performed at the $10^{th}$ thoracic vertebra (T10). The vertebral column was stabilized with angled clamps on the upper thoracic (T8) and lumbar (T11) levels and the impactor with a tip diameter of 2 mm was delivered at approximately 50 kd onto the exposed, intact dura overlying the dorsal spinal cord. The impactor was immediately removed, the wound irrigated with saline, and the muscle and skin openings sutured together. Female animals were used due to the paralysis associated with the injury and ease of voiding the bladder.

Following surgery, animals were placed in their home cage and dosing was initiated. Animals were treated with saline (Group 1: sham, Group 2: injured), PEG (Group 3: injured), magnesium (Group 4: injured) or a combination of PEG and magnesium solutions (Group 5: injured). The PEG solution was composed of PEG3350 at 30% in 0.5% saline (custom made by AAIPharma Developmental Services, Wilmington, N.C.). The magnesium solution was composed of magnesium sulfate at 50% in an injectable formulation (American Regent Laboratories, inc). The magnesium solution was diluted in saline 1:1 before intravenous injection as recommended by the manufacturer. In the cases of combined PEG+Mg combined treatments, animal received the PEG and magnesium components from two individual solutions.

In more details, each animal received 2 injections:
Group 1: Sham—1.79 ml/kg of Saline followed by 1.79 ml/kg of Saline;
Group 2: Injured—1.79 ml/kg of Saline followed by 1.79 ml/kg of Saline;
Group 3: Injured—3.33 ml/kg of PEG solution followed by 0.24 ml/kg of Saline;
Group 4: Injured—0.24 ml/kg of magnesium solution followed by 3.33 ml/kg of Saline;
Group 5: Injured—3.33 ml/kg of PEG solution followed by 0.24 ml/kg of magnesium solution.

The first two injections were administered 15 minutes following injury. Another round of two injections was given 6 hours later. The total dose of PEG and magnesium sulfate administered was of 2 and 0.12 g/kg (body weight) respectively. The compounds tested were administered by bolus intravenous injection. There was 9-10 animals/group. These studies were performed in a randomized and blinded fashion such as the solutions were sent to the Research Center in blindly labeled packages and the code was not revealed to the Research Center before the end of the study.

Assessment of Motor Function

To assess locomotor recovery after SCI, animals were tested prior to surgery and up to 6 weeks post-injury. Animals were placed in an open field chamber (120 cm diameter, 25 cm wall height) for 4 minutes to assure that all subjects obtained a maximum score of 12 using a modified version of the Basso, Beattie, and Bresnahan (BBB) locomotor rating scale (Ferguson et al., 2004). Rats were placed in the open field for 4 minutes and videotaped for scoring.

The rats in the SCI groups were subjected to anesthesia, laminectomy and controlled spinal impact delivered directly on the dura. The "sham" group underwent identical surgical procedures, but the surface of the spinal cord was not impacted. Following spinal cord injury, rats were treated with intravenous injections of saline, PEG, Magnesium or combined PEG and Magnesium solutions. All rats received two injection regiments, one fifteen minutes post-injury and another one 6 hours later. For the following 6 weeks post-injury, the animals were tested for their locomotor ability using a modified version of the Basso, Beattie, and Bresnahan (BBB) locomotor rating scale with a maximum score of 12 (Ferguson et al., 2004).

To evaluate the significance of difference between experimental groups, data were analyzed using an unpaired, two-tailed t statistical test with confidence intervals of 95%. Following laminectomy only (sham group) or laminectomy and controlled impact (SCI groups), the rats were treated with intravenous injections of saline, PEG or magnesium (Mg) solutions. Treatment with PEG alone or Mg alone had no effect on motor functions following SCI. In contrast, combined PEG and Mg treatments significantly improved locomotor recovery as evaluated by the 12-point BBB score relative to SCI-Saline group.

At the end of the study, the spinal cords were extracted and fixed in 4% paraformaldehyde. For analysis, 20 um cryosections were stained for eriochrome cyanine (EC) to differentiate between white matter and cell bodies to calculate the amount of spared tissue through the lesion site. Tissue sparing was determined by computed image analysis be from 10 evenly spaced sections through the injured T10 segment. The area of necrotic tissue was divided by the total cross-sectional area, converted to a percentage and subtracted from 100%.

Animals were sacrificed on day 14 and spinal cord tissues were processed to determine the lesion volume. Treatment with PEG reduced the lesion volume by 20% but this change was not statistically significant relative to the control group (SCI-Saline). Animals treated with Mg showed a significant reduction (33%) of the lesion volume as compared to control animals. Combined treatment with PEG and Mg solutions showed a positive and additive effect significantly decreasing the lesion volume by 51% relative to control group. Average lesion volume in the animal group that received the combined treatments was significantly reduced relative to animals treated with PEG alone (p=0.0393) or Mg alone (p=0.0364).

Example 5

Improved Motor Recovery Following Treatment with a Combination of PEG and Magnesium Compound Relative to PEG Alone or Magnesium Compound Alone in a SCI Dural Compression Model Animals Wistar female rats weighing 200-250 grams received a controlled clip-compression injury at T4. This experimental model has been previously described in details in Gris et al., 2004. Briefly, animals were premedicated with diazepam (3.5 mg/kg, i.p.) and atropine (0.05 mg/kg, s.c.) in order to facilitate a smooth induction of anesthesia by 4% halothane and maintenance with 1.0-1.5% halothane. The T4 spinal cord segment was exposed by dorsal laminectomy and a modified aneurysm clip, calibrated to 50 grams compression was passed extradurally around the cord and spring released for 60 seconds. Nerve roots were not disrupted during the clip compression.

Following SCI, animals were placed in their home cage and dosing was initiated. Animals were treated with saline, PEG, magnesium or combined PEG+magnesium solutions. The PEG solution was composed of PEG3350 at 30% in 0.5% saline (custom made by AAIPharma Developmental Services, Wilmington, N.C.). The magnesium solution was composed of magnesium sulfate at 50% in an injectable formulation (American Regent Laboratories, inc) further diluted in saline 0.5%. For the combined treatment, PEG and magnesium solutions were pre-mixed a few minutes before administration. Treatment solutions were administered by intravenous injections.

Each animal received 2 injections, the first one 15 minutes after injury and the second injection 6 hours later. The total dose of PEG and magnesium sulfate administered was of 2 and 0.6 g/kg (body weight) respectively. There was 6-10 animals/group. These studies were performed in a randomized and blinded fashion such as the solutions were sent to the Research Center in blindly labeled packages and the code was not revealed to the examiners before the end of the study.

Assessment of Locomotor Recovery

Locomotor recovery was assessed by the 21-point Basso, Beatie and Bresnahan (BBB) open field locomotor test (Basso et al., 1995), from day 3-21 after injury. Locomotor function was evaluated by 2 blinded investigators at each testing period.

To evaluate the significance of difference between experimental groups, data were analyzed using an unpaired, two-tailed t statistical test with confidence intervals of 95%. The Welch's modification was also used to analyze the motor recovery to take in account the significant variability in the control group.

Following SCI, rats were treated with saline, PEG, Mg or a combined solution of PEG and Mg. Locomotor recovery was assessed by the 21-point BBB score system from day 3-25 post-injury. In this particular paradigm, PEG had no significant effect on motor recovery within the first 3 weeks after injury. Some improvement was seen at day 7 post-CSI derived from Mg treatment. Animals that received the combined PEG+Mg treatment showed faster recovery with an average BBB score significantly higher than PEG or Mg groups at day 14 post-injury.

Example 6

Treatment with a Combination of PEG and Magnesium Compound but not with PEG Alone or with Magnesium Compound Alone Reduced Severity/Occurrence of Neuropathic Pain.

Animals

Animals were prepared as described in Example 3.

Assessment of Development of Neuropathic Pain

Animals were tested for the development of neuropathic pain before and up to 3 weeks post-injury. Neuropathic pain occurrence and severity was evaluated by the response of the animal to a stimulus that is normally not painful or allodynia. Briefly, a modified Semmes-Weinstein monofilament (Stoelting Co, Wood Dale, Ill.) calibrated to generate a force of 15 mN was applied to the dorsal trunk at dermatomes corresponding to spinal segments immediately rostral to the lesion level (T1-T3). The monofilament was applied 10 times for 3 seconds, with each stimulus being separated by a 5 second interval, and the number of avoidance responses out of a possible 10 were recorded. Avoidance responses were defined as flinching, escape, vocalization, or abnormal aggressive behaviors. The scoring system used to monitor mechanical allodynia has been presented in details in Gris et al., 2004. Mechanical allodynia testing was conducted twice per week and the 2 tests were averaged for each animal and reported as a weekly pain score.

To evaluate the significance of difference between experimental groups, data were analyzed using an unpaired, two-tailed t statistical test with confidence intervals of 95%. The Welch's modification was also used to analyze the motor recovery to take in account the significant variability in the control group.

In general, the score of a non-injured animal would be equal to zero. The number of avoidance responses of the SCI animals injected with saline increased progressively after injury to reach a mean pain score of 3.2+/−0.5 at week-3 post-injury consistent with the development of neuropathic pain. In this particular paradigm, PEG or Mg had no significant effect on the development of neuropathic pain after SCI. Combined treatment with PEG+Mg dramatically reduced the occurrence/severity of neuropathic pain to 1+/−0.6 and significantly lower than animals treated with saline.

Example 7

Treatment with a Combination of PEG and Magnesium Compound but not with PEG Alone or with Magnesium Compound Alone Reduced Severity of Pain in a Model of Acute Inflammation Animals Animals were treated with saline (0.5% final), indomethacin, PEG, magnesium or combined PEG+magnesium solutions. Each animal received 2 injections, the first one 1 hour following carrageenan injection and the second injection 6 hours later. The total dose of PEG and magnesium chloride administered was of 2 and 0.135 g/kg (body weight) respectively. There were 10 animals per group. These studies were performed in a randomized and blinded fashion such as the solutions were sent to the Research Center in blindly labeled packages and the code was never revealed to the examiners.

Indomethacin (Fluka, cat. 57413, lot 450544/1) was dissolved in 25% hydroxyl-propyl beta cyclodextrin (hpBCD) by gentle heating and stirring. The PEG solution was composed of PEG3350 at 30% in 0.5% saline, the magnesium solution was composed of magnesium chloride at 2% and the combined PEG+magnesium solution was composed of 30% PEG3350+2% Magnesium Chloride (custom made by AAIPharma Developmental Services, Wilmington, N.C.).

Assessment of Pain

The carrageenan model (Iadarola et al., 1988) was used to induce hind paw acute inflammation. Male Sprague-Dawley (258±2.2 g) were anesthetized with isoflurane, and 50 µL of 2% λ-carrageenan (w/v; Sigma, catalog #C-3889, lot #122K1444) was injected intradermally into the left hind paw using a 1 cc syringe fitted with a 27 g needle. For the sham group, 50 µL of 0.9% saline was injected into the hind paw in an identical manner.

Twenty-four hours following carrageenan injection into the left paw, the same paw was tested for mechanical allodynia. Baseline and post-treatment values for non-noxious mechanical sensitivity were evaluated using 8 Semmes-Weinstein filaments (Stoelting, Wood Dale, Ill., USA) with varying stiffness (0.4, 0.7, 1.2, 2.0, 3.6, 5.5, 8.5, and 15 g) according to the up-down method (Chaplan et al., 1994). Animals were placed on a perforated metallic platform and allowed to acclimate to their surroundings for a minimum of 30 minutes before testing.

To evaluate the significance of difference between experimental groups, data were analyzed using an unpaired, two-tailed t statistical test with confidence intervals of 95%.

The mean pain score in the carrageenan-saline group was 3.4+/−0.5 and significantly lower (p<0.001) than the mean pain score of the sham (saline-saline group) animals evaluated at 12.7+/−1.1. In this carrageenan-paradigm, treatment with PEG or Magnesium had no significant effect on the pain score relative to animals treated with saline. Combined treatment with PEG+Mg significantly improved the pain score to 7.3+/−1.5 (p<0.05) relative to the carrageenan-saline group (3.4+/−0.5). PEG+Mg combined treatment was also significantly better than treatment with Mg alone (p<0.05). Indomethacin is a nonsteroidal anti-inflammatory drug that is approved by the FDA to relieve pain associated with inflammatory conditions. The combined PEG+Magnesium formulation led to a better pain score (7.3+/−1.5) than the animals treated with Indomethacin (5.6+/−0.9).

All patent and non-patent publications cited in this disclosure are incorporated herein in to the extent as if each of those patent and non-patent publications was incorporated herein by reference in its entirety. Further, even though the invention herein has been described with reference to particular examples and embodiments, it is to be understood that these examples and embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. An intravenous pharmaceutical composition for treating a neuronal injury comprising a therapeutically effective amount of a biomembrane sealing agent comprising between 20 and 50% w/w of polyethylene glycol and at least one magnesium compound, wherein the polyethylene glycol comprises PEG 3350.

2. The pharmaceutical composition of claim 1, wherein the at least one magnesium compound is a magnesium salt.

3. The pharmaceutical composition of claim 1 wherein the at least one magnesium compound is selected from the group consisting of magnesium sulfate, magnesium chloride, magnesium gluconate, magnesium ATP, and any combination thereof.

4. The pharmaceutical composition of claim 1, wherein the at least one magnesium compound is selected from the group consisting of magnesium sulfate, magnesium chloride, and any combination thereof.

5. The pharmaceutical composition of claim 1, which is incapable of forming a gel.

6. A formulation comprising the pharmaceutical composition of claim 1.

7. The formulation of claim 6, which is a sustained release formulation.

8. A method of treating a pathological condition, selected from the group consisting of a neuronal injury, a tissue injury, a surgical intervention, and any combination thereof, the method comprising delivering to a subject in need thereof a therapeutically effective amount of an injectable pharmaceutical composition according to claim 1.

9. The method of claim 8, wherein the neuronal injury is selected from the group consisting of an injury to the central nervous system, an injury to the peripheral nervous system, an injury to the cranial nerves, an injury to the optical nerve and any combination thereof.

10. The method of claim 8 wherein the therapeutically effective amount of at least one biomembrane sealing agent and the therapeutically effective amount of at least one magnesium compound are delivered by a delivery method selected from the group consisting of an intravenous administration, an intramuscular administration, an intrathecal administration, a subcutaneous administration, an epidural administration, a parenteral administration, an intraarticular administration, a direct application or deposition onto or adjacent to a site of the pathological condition, and any combinations thereof.

11. The method of claim 8 wherein the therapeutically effective amount of at least one biomembrane sealing agent and the therapeutically effective amount of at least one magnesium compound are delivered an intravenous administration.

12. The method of claim 8 wherein the injectable composition is incapable of forming a gel.

13. A kit for intravenously injecting a pharmaceutical composition to treat a neuronal injury, comprising:
a therapeutically effective amount of a biomembrane sealing agent comprising polyethylene glycol;
at least one magnesium compound; and
a set of instructions comprising information on making an injectable composition, comprising between 20 and 50% w/w of the polyethylene glycol, wherein the polyethylene glycol comprises PEG 3350.

14. The kit of claim 13, wherein the at least one magnesium compound is a magnesium salt.

15. The kit of claim 13 wherein the at least one magnesium compound is selected from the group consisting of magnesium sulfate, magnesium chloride, magnesium gluconate, magnesium ATP, and any combination thereof.

16. The kit of claim 13, wherein the at least one magnesium compound is selected from the group consisting of magnesium sulfate, magnesium chloride, and any combination thereof.

17. The kit of claim 13, wherein the pharmaceutical composition is incapable of forming a gel.

18. A method of accelerating tissue healing or reducing scar formation comprising:
administering to a subject in need thereof an injectable pharmaceutical composition according to claim 1.

19. The method of claim 18, wherein the injury comprises a traumatic injury.

20. The method of claim 18, wherein the injury comprises an interventional injury.

21. The method of claim 18, wherein the therapeutically effective amount of at least one biomembrane sealing agent and the therapeutically effective amount of at least one magnesium compound are administered by a method selected from the group consisting of an intravenous administration, an intramuscular administration, an intrathecal administration, a subcutaneous administration, an epidural administration, a parenteral administration, an intra-articular administration, a direct application or deposition onto or adjacent to a site of the pathological condition, and any combination thereof.

22. The method of claim 18, wherein the at least one biomembrane agent and the at least one magnesium compound are administered independently of each other.

23. The method of claim 18, wherein the at least one biomembrane sealing agent and the at least one magnesium compound are combined before the step of administering the at least one biomembrane sealing agent and the at least one bioactive agent to the subject in need thereof.

24. The method of claim 18, wherein the at least one biomembrane sealing agent or the at least one magnesium compound is administered from an implant selected from the group consisting of depot, pump, sustained release preparations or any combinations thereof.

25. The method of claim 18, further comprising the step of administering at least one marker with the at least one biomembrane sealing agent or the at least one magnesium compound.

26. The method of claim 18, wherein the at least one biomembrane sealing agent is selected from the group consisting of polyethylene glycol (PEG), block polymers, poloxamers and combinations thereof.

27. The method of claim 18, wherein the at least one magnesium compound is selected from the group consisting of magnesium sulfate, magnesium chloride, magnesium gluconate, magnesium ATP, and any combination thereof.

28. The method of claim 18 further comprising administering to a subject in need thereof a therapeutically effective amount of at least one bioactive agent.

29. The method of claim 28, wherein the at least one bioactive agent is selected from the group consisting of analgesics, neurotransmitter and receptor modulators; anti-inflammatory agents; antioxidants; anti-apoptotic agents; neurotropic and growth agents; modulators of lipid formation and transport; modulators of blood flow and vessel formation; and any combinations thereof.

30. The pharmaceutical composition of claim 1, wherein the composition does not contain any COX inhibitor.

31. The kit of claim 13, wherein the pharmaceutical composition does not contain any COX inhibitor.

32. The pharmaceutical composition of claim 1, wherein the biomembrane sealing agent comprises about 30 to about 50% w/w of polyethylene glycol.

33. The pharmaceutical composition of claim 1, wherein the biomembrane sealing agent comprises about 20% w/w of polyethylene glycol.

34. The pharmaceutical composition of claim 1, wherein the biomembrane sealing agent comprises about 30% w/w of polyethylene glycol.

35. The pharmaceutical composition of claim 1, wherein the pharmaceutical composition comprises an antioxidant.

36. The pharmaceutical composition of claim 1, wherein the polyethylene glycol comprises 30% w/w of the pharmaceutical composition.

37. The pharmaceutical composition of claim 1, wherein the pharmaceutical composition comprises an antioxidant and the polyethylene glycol comprises 30% w/w of the pharmaceutical composition.

38. The pharmaceutical composition of claim 1, wherein the pharmaceutical composition is used to treat traumatic brain injury.

39. The pharmaceutical composition of claim 1, wherein the pharmaceutical composition is used to treat spinal cord injury.

40. The pharmaceutical composition of claim 1, wherein the pharmaceutical composition is used to treat injury from a stroke.

41. The pharmaceutical composition of claim 1, wherein the pharmaceutical composition is used to treat ischemic stroke.

42. The pharmaceutical composition of claim 1, wherein the pharmaceutical composition is used to treat hemorrhagic stroke.

43. The pharmaceutical composition of claim 1, wherein the pharmaceutical composition is used to treat cranial nerve injury.

44. The pharmaceutical composition of claim 1, wherein the pharmaceutical composition is used to treat peripheral nerve injury.

45. The pharmaceutical composition of claim 1, wherein the at least one magnesium compound comprises more than 0.1% w/v of the composition.

46. The pharmaceutical composition of claim 1, wherein the at least one magnesium compound comprises magnesium chloride.

47. The kit of claim 13, wherein the at least one magnesium compound comprises magnesium chloride.

48. A method of treating a pathological condition selected from the group consisting of a neuronal injury, a tissue injury, a surgical intervention, and any combination thereof, the method comprising delivering to a subject in need thereof a therapeutically effective amount of at least one biomembrane sealing agent and a therapeutically effective amount of an injectable pharmaceutical composition according to claim 1.

49. The method of claim 48, wherein neuronal injury is selected from the group consisting of an injury to the central nervous system, an injury to the peripheral nervous system, an injury to the cranial nerves, an injury to the optical nerve and any combination thereof.

50. The method of claim 48 wherein the therapeutically effective amount of at least one biomembrane sealing agent and the therapeutically effective amount of at least one bioactive agent are delivered by a delivery method selected from the group consisting of an intravenous administration, an intramuscular administration, an intrathecal administration, a subcutaneous administration, an epidural administration, a parenteral administration, an intraarticular administration, a direct application or deposition onto or adjacent to a site of the pathological condition, and any combinations thereof.

51. The method of claim 48 wherein the therapeutically effective amount of at least one biomembrane sealing agent and the therapeutically effective amount of at least one bioactive agent are delivered by intravenous administration.

52. The method of claim 48, wherein the at least one biomembrane agent and at least one bioactive agent are delivered independently of each other.

53. The method of claim 48, wherein the at least one biomembrane sealing agent and the at least one bioactive agent are combined before the step of delivering the at least one biomembrane sealing agent and the at least one bioactive agent to the subject in need thereof.

54. The method of claim 48, wherein the at least one biomembrane sealing agent or the at least one bioactive agent are delivered from an implant.

55. The method of claim 48 wherein the at least one biomembrane sealing agent or the at least one bioactive agent are delivered from a pump.

56. The method of claim 48, further comprising the step of delivering at least one marker with the at least one biomembrane sealing agent or the at least one bioactive agent.

57. The method of claim 48, wherein at least one compound is delivered prior to an occurrence of the pathological condition, said one compound selected from the group consisting of the at least one biomembrane sealing agent and the at least one bioactive agent.

58. The method of claim 48, wherein the composition is incapable of forming a gel.

* * * * *

UNITED STATES PATENT AND TRADEMARK OFFICE
CERTIFICATE OF CORRECTION

PATENT NO. : 8,945,623 B2
APPLICATION NO. : 11/418152
DATED : February 3, 2015
INVENTOR(S) : Roy et al.

It is certified that error appears in the above-identified patent and that said Letters Patent is hereby corrected as shown below:

On the title page item (56), under "OTHER PUBLICATIONS", in Column 2, Line 27, delete "polyetheylene" and insert -- polyethylene --, therefor.

On the title page item (56), under "OTHER PUBLICATIONS", in Column 2, Line 30, delete "cinically" and insert -- clinically --, therefor.

In the Specification,

In Column 4, Line 66, delete "amphipatic" and insert -- amphipathic --, therefor.

In Column 7, Line 54, delete "anti-apoptotoc" and insert -- anti-apoptotic --, therefor.

In Column 9, Lines 43-44, delete "(Nyocomed," and insert -- (Nycomed, --, therefor.

In Column 9, Line 44, delete "gandolinium-based" and insert -- gadolinium-based --, therefor.

In Column 9, Line 45, delete "gadodiaminde," and insert -- gadodiamide, --, therefor.

In Column 10, Lines 17-18, delete "poly-(methylmethacylate)" and insert -- polymethylmethacrylate) --, therefor.

In Column 10, Line 66, delete "(Nyocomed," and insert -- (Nycomed, --, therefor.

In Column 10, Line 67, delete "gandolinium-based" and insert -- gadolinium-based --, therefor.

In Column 11, Line 1, delete "gadodiaminde," and insert -- gadodiamide, --, therefor.

In Column 12, Line 8, delete "postherapeutic" and insert -- postherpetic --, therefor.

Signed and Sealed this
Seventh Day of July, 2015

Michelle K. Lee
*Director of the United States Patent and Trademark Office*

In Column 13, Line 3, delete "isoflorane" and insert -- isoflurane --, therefor.

In the Claims,

In Column 24, Line 16, in Claim 57, delete "wherein at least" and insert -- wherein the at least --, therefor.